United States Patent [19]

Katsuda

[11] 3,968,238

[45] July 6, 1976

[54] 5-ACETYL FURFURYLESTER OF CHRYSANTHEMUMIC ACID

[75] Inventor: Yoshio Katsuda, Osaka, Japan

[73] Assignee: Dainippon Jochugiku Kabushiki Kaisha, Osaka, Japan

[22] Filed: July 30, 1975

[21] Appl. No.: 600,425

Related U.S. Application Data

[60] Division of Ser. No. 399,418, Sept. 21, 1973, which is a division of Ser. No. 112,061, Feb. 2, 1971, Pat. No. 3,796,730, which is a continuation-in-part of Ser. Nos. 691,173, Dec. 18, 1967, abandoned, and Ser. No. 809,036, March 20, 1969, abandoned, which is a division of Ser. No. 629,422, April 10, 1967, abandoned, and a continuation-in-part of Ser. No. 691,173.

[30] Foreign Application Priority Data

| June 28, 1966 | Japan | 41-42289 |
| Aug. 24, 1966 | Japan | 41-55930 |
| Dec. 23, 1966 | Japan | 41-84365 |

[52] U.S. Cl. ............................ 424/285; 260/347.4
[51] Int. Cl.$^2$ ...................................... C07D 307/12
[58] Field of Search ................... 260/347.4; 424/285

[56] References Cited

UNITED STATES PATENTS 3,465,007  9/1969  Elliot ............................. 260/347.4

*Primary Examiner*—Henry R. Jiles
*Assistant Examiner*—Bernard Dentz
*Attorney, Agent, or Firm*—Joseph F. Brisebois

[57] ABSTRACT

The present invention relates to 5 acetyl furfurylester of chrysanthemumic acid, a new substituted furfurylesters of chrysanthemumic acid which have improved insecticidal properties.

5 Claims, No Drawings

5-ACETYL FURFURYLESTER OF CHRYSANTHEMUMIC ACID

This is a division of application Ser. No. 399,418, filed Sept. 21, 1973, which was a division of Ser. No. 112,061, filed Feb. 2, 1971, now U.S. Pat. No. 3,796,730, which was a continuation-in-part of Ser. No. 691,173, filed Dec. 18, 1967, now abandoned, and Ser. No. 809,036, filed Mar. 20, 1969, now abandoned, which was itself a continuation-in-part of Ser. No. 691,173 and a divisional of Ser. No. 629,422, filed Apr. 10, 1967, now abandoned.

SUMMARY OF THE INVENTION

The present invention relates to an insecticide containing as its active ingredient 5-acetylfurfurylester of chrysanthemumic acid.

After repeated studies of insecticides containing as their active ingredient an ester of chrysanthemumic acid, the present inventor discovered that the compound listed above as the insecticidal ingredient of insecticides for dusting and fumigating application is highly effective on agricultural and horticultural plants, and that it has very low toxicity for killing various insects on humans and animals and on warm-blooded animals.

The present invention is based on this discovery. This compound adopted as the active ingredient of the insecticide of this invention can be easily obtained by reacting the corresponding substituted furfuryl alcohol, its halide or its salts containing the above-mentioned substituents with, say, chrysanthemumic acid, or its halide, anhydride, ester, or its salts, according to the general process for producing ester of chrysanthemumic acid as disclosed in U.S. patent application Ser. No. 629,422, filed on Apr. 10, 1967, now abandoned and Ser. No. 809,036, filed Mar. 20, 1969, now abandoned by the present inventor, described below.

The substituted furfurylester of chrysanthemumic acid of this invention as expressed by formula (I):

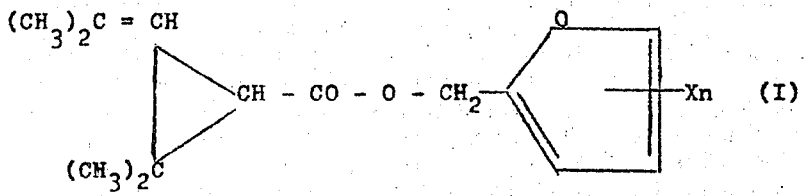 (I)

where X represents a substitutent selected from the group consisting of alkyl having 1 to 6 carbon atoms, alkenyl having 2 to 6 carbon atoms, alkynyl having 2 to 6 carbon atoms, phenyl alkyl having 1 to 6 carbon atoms in the alkyl group, alkoxy having 1 to 6 carbon atoms, alkenyloxy having 2 to 6 carbon atoms, alkoxyalkyl having 2 to 12 carbon atoms, alkenyloxyalkyl having 3 to 12 carbon atoms, RCO— where R stands for an aliphatic hydrocarbon or phenyl having 1 to 6 carbon atoms, alkoxyalkoxyalkyl having 3 to 18 carbon atoms, cyclopentadienyl, halogen, nitro, and amino; and $n$ is an integer selected from 1 to 3, having an extremely strong insecticidal effect on insects, particularly on araeopidae, jassidas and aphididae, can be manufactured by the following methods:

1. a substituted furfurylalcohol as expressed by the following formula:

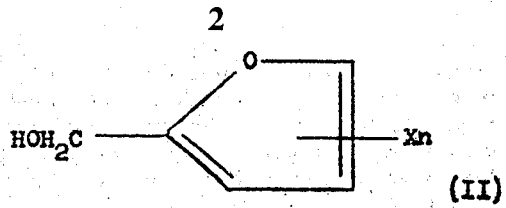 (II)

where X represents a substituent selected from the group consisting of alkyl having 1 to 6 carbon atoms, alkenyl having 2 to 6 carbon atoms, alkynyl having 2 to 6 carbon atoms, phenyl alkyl having 1 to 6 carbon atoms, alkoxy having 1 to 6 carbon atoms, alkenyloxy having 2 to 6 carbon atoms, alkoxyalkyl having 2 to 12 carbon atoms, alkenyloxyalkyl having 3 to 12 carbon atoms, RCO— where R stands for aliphatic hydrocarbon or phenyl having 1 to 6 carbon atoms, alkoxyalkoxyalkyl having 3 to 18 carbon atoms, cyclopentadienyl, halogen, nitro, and amino; and $n$ is an integer selected from 1 to 3, is reacted with chrysanthemumic acid or its functional derivative salts and esters which react to liberate chrysanthemumic acid for this reaction. The abovementioned substituted furfurylalcohol can be treated with an alkali metal such as sodium or potassium, and then, as an alcoholate, may be reacted with the above-mentioned chrysanthemumic acid or its functional derivative.

2. Said substituted furfurylesters of chrysanthemumic acid can be obtained by treating the substituted furfurylalcohol of the above formula (II) with a salt, such as thionylchloride, phosphorus pentachloride, etc., and reacting the resultant substituted furfurylchloride with chrysanthemumic acid or its salts.

3. Said substituted furfurylesters of chrysanthemumic acid can be obtained by reacting an ester of the substituted furfurylalcohol as expressed by the above formula (II) and an organic acid such as acetic acid or propionic acid with chrysanthemumic acid or its ester.

In the above-mentioned methods, the term "functional derivative of chrysanthemumic acid" may be illustrated by the acid halides such as acid chlorides or acid bromides; acid anhydrides; esters such as methyl ester, ethyl ester, etc.; and salts such as alkali metal salts, silver salts, lead salts, etc. of chrysanthemumic acid; and the term "salts and esters of chrysanthemumic acid" refers to similar salts and esters as mentioned above.

As examples of the substituted furfurylalcohols expressed by the above formula (II), the following illustrative examples may be mentioned:

5-methyl furfuryl alcohol; 3-allyl furfuryl alcohol; 4-allyl furfuryl alcohol; 5-allyl furfuryl alcohol; 3-nitro-5-ethoxy furfuryl alcohol; 3,4-dichloro-5-allyloxy furfuryl alcohol; 4-hexyl-5-pentyloxy furfuryl alcohol; 3,4-dimethyl-5-allyl furfuryl alcohol; 3,4-dichloro-5-ethyl furfuryl alcohol; 5-bromo-furfuryl alcohol, 5-ethoxy furfuryl alcohol; 5-propargyl furfuryl alcohol;

3-methyl-5-propargyl furfuryl alcohol; 4-methyl-5-propargyl furfuryl alcohol; 3-methoxy-5-propargyl furfuryl alcohol; 3,4-dichloro-5-propargyl furfuryl alcohol; 5-ethoxymethyl furfuryl alcohol; 5-acetyl furfuryl alcohol; 5-allyloxymethyl furfuryl alcohol; 3,4-dichloro-5-benzyl furfuryl alcohol; 5-benzoyl furfuryl alcohol; 5-(2'-butenyl) furfuryl alcohol; 5-(2'-butinyl) furfuryl alcohol; 5-methoxymethoxymethyl furfuryl alcohol; 3-amino-5-allyl furfuryl alcohol; 5-benzyl furfuryl alcohol; etc.

Typical esters of chrysanthemumic acid are:
1. 3,4-dichloro-5-propargylfurfurylester of chrysanthemumic acid
2. 3,4-dibromo-5-cyclopentadienylfurfurylester of chrysanthemumic acid
3. 5-ethoxymethylfurfurylester of chrysanthemumic acid
4. 3-acetyl-5-allyloxyfurfurylester of chrysanthemumic acid
5. 5-allyloxymethylfurfurylester of chrysanthemumic acid
6. 3,4-dimethyl-5-allylketofurfurylester of chrysanthemumic acid
7. 3-acetyl-5-allylfurfurylester of chrysanthemumic acid
8. 5-acetylfurfurylester of chrysanthemumic acid
9. 5-methoxyallylfurfurylester of chrysanthemumic acid
10. 5-allyloxyvinylfurfurylester of chrysanthemumic acid
11. 3,4-dichloro-5-benzylfurfurylester of chrysanthemumic acid
12. 5-phenylvinylfurfurylester of chrysanthemumic acid
13. 3-methyl-5-methylketoallylfurfurylester of chrysanthemumic acid
14. 5-methoxypropoxymethylfurfurylester of chrysanthemumic acid
15. 5-propargylfurfurylester of chrysanthemumic acid
16. 3-methoxy-5-propargylfurfurylester of chrysanthemumic acid
17. 3-methyl-5-propargylfurfurylester of chrysanthemumic acid These esters according to this invention, when practically employed as the active ingredients in insecticidal sprays, are usually blended with some suitable conventional insecticidal carrier and may be used in the form of a powder, wettable powder, tablets, solution, emulsion, aerosol, etc.

For instance, these esters can be evenly mixed with granular inert carriers such as talc, clay, bentonite, kaoline, and diatomaceous earth, and made into a wettable powder.

Or they may be mixed with both the above-mentioned granular inert carriers and with surface-active agents; and then kneaded and crushed into a wettable powder.

They may also be diluted with the above-mentioned inert carriers mixed with starch, sodium alginate, or natural binders such as CMC or PVA; and then stamped into tablets. Adequate quantities of these esters may also be dissolved in such solvents as kerosene to form solutions. These esters may likewise be dissolved in such solvents as xylole, benzene, etc., mixed with a surface-active agent, and made into emulsions.

In addition, they may be dissolved with other insecticides, adjuvants, perfumes, etc., in kerosene and the resulting aerosol may be compressed with a pressure vessel and sealed therein together with such propellants as freon, vinylchloride, LPG, etc. so as to produce aerosol preparations.

When these esters are to be employed as insecticides for fumigation, they can be mixed with some appropriate base such as powdered wood and used in the form of mosquito incense sticks. If they are to be used as insecticides for heating and evaporating use, they are dissolved in, say, white kerosene and the resulting solution is continuously fed onto the evaporating surface of an electric heater or said solution is absorbed into a carrier consisting of a noninflammable material such as asbestos and the resulting product heated on an electric heater.

The concentration of these esters in the insecticides according to this invention depends on the form of preparation, the manner of use, the objective of use, etc. The preferred range of concentration would be 0.05–60%. However, their concentration is not necessarily limited to this range, but may be varied over a wider range. For long time use, a low concentration is preferred, while for short time use a high concentration may be possible.

Moreover, the insecticidal power of said esters of chrysanthemumic acid will be further enhanced, when they are combined with such synergists as N-octylbicycloheptenedicarboxyimide; mixtures of N-octylbicycloheptenedicarboxyimide and the isopropylamine salt of dodecyl benzene sulfonic acid; octachlorodipropylether; piperonylbutoxide; etc.

An illustrative example of the synthesis of the substituted furfurylesters of chrysanthemumic acid of this invention will now be given:

EXAMPLE 1

2.2g of 5-allylfurfurylalcohol is dissolved in 15 ml of dry benzene and the resulting substance is mixed with 3 g of chrysanthemumic acid chloride dissolved in dry benzene, and with 2 ml of dry pyridine as a condensation agent. This procedure yields crystals of pyridine hydrochloride. These crystals are sealed up and left at room temperature overnight, and the pyridine hydrochloride is then separated by filtering. The benzene solution is then washed successively with aqueous sodium bicarbonate, dilute hydrochloric acid and water. When this benzene solution is dried and then condensed in a nitrogen flow under lowered pressure at a low temperature (below 50°C of bath temperature), 4g of viscous, transparent 5-allylfurfurylester of chrysanthemumic acid is obtained. The yield is almost constant, boiling point being 129°–130°C/0.35mmHg, $n_D^{25}$ : 1.4948.

EXAMPLE 2

In the same way as Example 1, 2.5g of 5-acetylfurfurylalcohol is reacted with 5.5g of chrysanthemumic acid bromide producing 4.3g of 5-acetylfurfurylester of chrysanthemumic acid. Bp: 126°–130°C/0.25mmHg.

The following examples illustrate some of the insecticidal effects of the substituted esters of chrysanthemumic acid of this invention.

Test (1) Spraying test

A 0.5% white kerosene solution of test insecticide was applied on house flies in accordance with the modified Campbell and Sullivan's metal turn table method and from the knock down rate of the flies, the relative effectiveness of insecticides have been calculated. The number indicated in the column of test insecticides corresponds to that mentioned in the said enumeration of esters as active ingredient.

| Test insecticides | Probit 4 | Probit 5 | Probit 6 |
|---|---|---|---|
| 3% white kerosene solution of furfurylesters of chrysanthemumic acid | 1.00 | 1.00 | 1.00 |
| 1 | 1.45 | 1.50 | 1.56 |
| 2 | 2.12 | 2.15 | 2.19 |
| 7 | 2.52 | 2.58 | 2.65 |
| 9 | 1.72 | 1.79 | 1.85 |
| 13 | 1.43 | 1.46 | 1.51 |
| 16 | 3.57 | 3.62 | 3.70 |
| 17 | 3.42 | 3.50 | 3.57 |

Test (2) Fumigation Test

A mosquito incense coil containing 0.5% of insecticidal ingredient was prepared and applied to knock down the adults of culex pipiens pallens Coquillett. This test was carried out in accordance with the procedure proposed by Nagasawa, Katsuda et al. in "Bochyu-Kagaku (insecticidal Science)" Vol. 16 (1951), P. 176.

The relative effectiveness of test mosquito coils (with the number corresponding to that in the said enumeration of esters as actice ingredient) thus calculated are as follows:

| Test insecticides | Probit 4 | Probit 5 | Probit 6 |
|---|---|---|---|
| Mosquito incense coil containing 3% furfurylester of chrysanthemumic acid | 1.00 | 1.00 | 1.00 |
| 1 | 1.58 | 1.65 | 1.70 |
| 2 | 2.35 | 2.40 | 2.44 |
| 4 | 1.43 | 1.49 | 1.53 |
| 6 | 1.81 | 1.87 | 1.95 |
| 7 | 2.83 | 2.89 | 2.94 |
| 15 | 3.54 | 3.59 | 3.61 |

All of the compounds mentioned as the active ingredient of this invention have high vapour pressure and accordingly can be vaporized more easily by heating than the conventional pyrethroids.

Therefore, less subject to thermal decomposition and giving an extremely high rate of dispersion, said compounds exhibit a notably remarkable effect in a mosquito incense coil ("electric mosquito incense", as provisionally called) which must be heated to be effective.

When the conventional pyrethroids like natural pyrethrin or allethrin are used in the vaporizer such as a mosquito incense coil or an electric mosquito incense, the dispersion rate of the active ingredient is a mere 15% or so, the greater part of the balance failing to be dispersed in the air. By contrast, when a mosquito incense coil was manufactured using the active ingredient of this invention in accordance with the traditional method, the dispersion rate of the active ingredient as measured in its smoke amounted to 30–40%. Meanwhile, when the same active ingredient was impregnated into a base mat or was absorbed on an appropriate extending agent and molded or was dissolved into a solvent and was then heated and vaporized by an adequate heater, this being the so-called electric mosquito incense process, as good a dispersion rate as in the case of a plain mosquito incense coil could be secured.

This shows that the active ingredient of this invention, when applied under fumigation and heating, can exhibit a particularly excellent insecticidal effect by its superb power and its high dispersibility. Thereby, it is possible to use the present active ingredient together with the conventional pyrethroids to obtain a synergistic effect and enhance the significance of this invention.

Some illustrative insecticide compositions of this invention are listed below.

EXAMPLE 3

0.2 part of 3-acetyl-5-allylfurfurylester of chrysanthemumic acid was dissolved in white kerosene, producing a 0.2% kerosene preparation with the whole solution as 100 parts.

EXAMPLE 4

A kerosene preparation was obtained by dissolving 0.3 part of 3-methyl-5-propargylfurfurylester of chrysanthemumic acid and 0.9 part of piperonylbutoxide into white kerosene, making 100 parts of the whole solution.

EXAMPLE 5

A mosquito incense coil containing 0.5% active ingredient was prepared in accordance with a known process by uniformly blending 0.5g of 5-propargylfurfurylester of chrysanthemumic acid with 99.5 g of a carrier base material like extract powder of pyrethrum, wood powder, starch, etc.

EXAMPLE 6

A mosquito incense coil containing 0.4% active ingredient was prepared in accordance with a known process by uniformly blending 0.4g of 5-propargylfurfurylester of chrysanthemumic acid and 1.0 g of a mixture (Tradename: MGK-5026) with 98.6g of a carrier base material like extract powder of pyrethrum, wood powder, starch, etc.

EXAMPLE 7

A mosquito incense coil was prepared using 0.3g of allethrin, 0.4g of 3-methoxy-5-propargylfurfurylester of chrysanthemumic acid and 99.3g of base material.

What is claimed is:

1. 5-acetylfurfurylester of chrysanthemumic acid.
2. An insecticide composition comprising an insecticidal amount of a compound of claim 1 and a carrier.
3. The composition of claim 2 which also contains a compound selected from the group consisting of N-octylbicycloheptene-dicarboxyimide, octachlorodipropylether and piperonylbutoxide.
4. The composition of claim 2 which also contains N-octylbicycloheptenedicarboxyimide and the isopropylamine salt of dodecyl benzene sulfonic acid.
5. The method of destroying noxious insects which comprises the step of applying to said insects an insecticidal amount of the composition of claim 2.

* * * * *